United States Patent
Nachum

(10) Patent No.: US 6,941,173 B2
(45) Date of Patent: *Sep. 6, 2005

(54) METHOD FOR THE TREATMENT OF BEDSORES USING ELECTRICAL IMPULSES

(75) Inventor: Zvi Nachum, Tiberias (IL)

(73) Assignee: Lifewave Ltd., Tel Aviv (IL)

( * ) Notice: Subject to any disclaimer, the term of this patent is extended or adjusted under 35 U.S.C. 154(b) by 173 days.

This patent is subject to a terminal disclaimer.

(21) Appl. No.: 10/240,715

(22) PCT Filed: May 30, 2001

(86) PCT No.: PCT/IL01/00502

§ 371 (c)(1),
(2), (4) Date: Oct. 4, 2002

(87) PCT Pub. No.: WO01/91697

PCT Pub. Date: Dec. 6, 2001

(65) Prior Publication Data

US 2003/0050675 A1 Mar. 13, 2003

Related U.S. Application Data

(63) Continuation of application No. 09/584,488, filed on Jun. 1, 2000, now Pat. No. 6,393,326, and a continuation of application No. 09/593,399, filed on Jun. 14, 2000, now Pat. No. 6,363,284.

(30) Foreign Application Priority Data

Jan. 3, 2001 (IL) .................................................. 140709

(51) Int. Cl.[7] .............................................. A61N 1/18
(52) U.S. Cl. ................................ 607/50; 60/46; 60/74; 60/73; 128/898
(58) Field of Search .............................. 607/50, 46, 72, 607/74, 73

(56) References Cited

U.S. PATENT DOCUMENTS

| 4,117,846 A | 10/1978 | Williams |
| 4,619,252 A | 10/1986 | Ibbott |

(Continued)

FOREIGN PATENT DOCUMENTS

| WO | WO97/01372 | 1/1997 |
| WO | WO99/04852 | 2/1999 |

OTHER PUBLICATIONS

Baker et al., "Effects of Electrical Stimulation on Wound Healing in Patients with Diabetic Ulcers," Diabetes Care: 20(3), 405–412 (Mar. 1997).*

*Primary Examiner*—Jeffrey R. Jastrzab
*Assistant Examiner*—Alyssa M. Alter
(74) *Attorney, Agent, or Firm*—Mark M. Friedman

(57) ABSTRACT

A method for the treatment of a sore by applying a series of voltage wave forms, including the steps of: (a) situating a pair of spaced-apart electrodes in contact with healthy tissue on opposite sides of a sore having substantially zero electrical activity, and (b) externally inducing a percutaneous flow of electrical current between the electrodes by establishing the series of voltage wave forms across the electrodes, wherein the series of voltage wave forms includes wave forms designed to substantially mimic characteristic natural voltage wave form emissions of at least one electrically activity sore. The sore can subsequently be monitored for independent electrical activity, and if independent electrical activity is not sustained, step (b) is reapplied. The treatment method is particularly appropriate for bedsores.

28 Claims, 10 Drawing Sheets

U.S. PATENT DOCUMENTS

| | | |
|---|---|---|
| 4,738,250 A | 4/1988 | Fulkerson et al. |
| 4,846,181 A | 7/1989 | Miller |
| 4,895,154 A | 1/1990 | Bartelt et al. |
| 4,919,138 A | 4/1990 | Nordenstroom |
| 4,982,742 A | 1/1991 | Claude |
| 5,158,081 A * | 10/1992 | McWhorter et al. .......... 607/50 |
| 5,218,973 A | 6/1993 | Weaver et al. |
| 5,395,398 A | 3/1995 | Rogozinski |
| 6,334,069 B1 * | 12/2001 | George et al. ................. 607/2 |
| 6,363,284 B1 * | 3/2002 | Nachum ...................... 607/50 |
| 6,393,326 B1 * | 5/2002 | Nachum ...................... 607/50 |

* cited by examiner

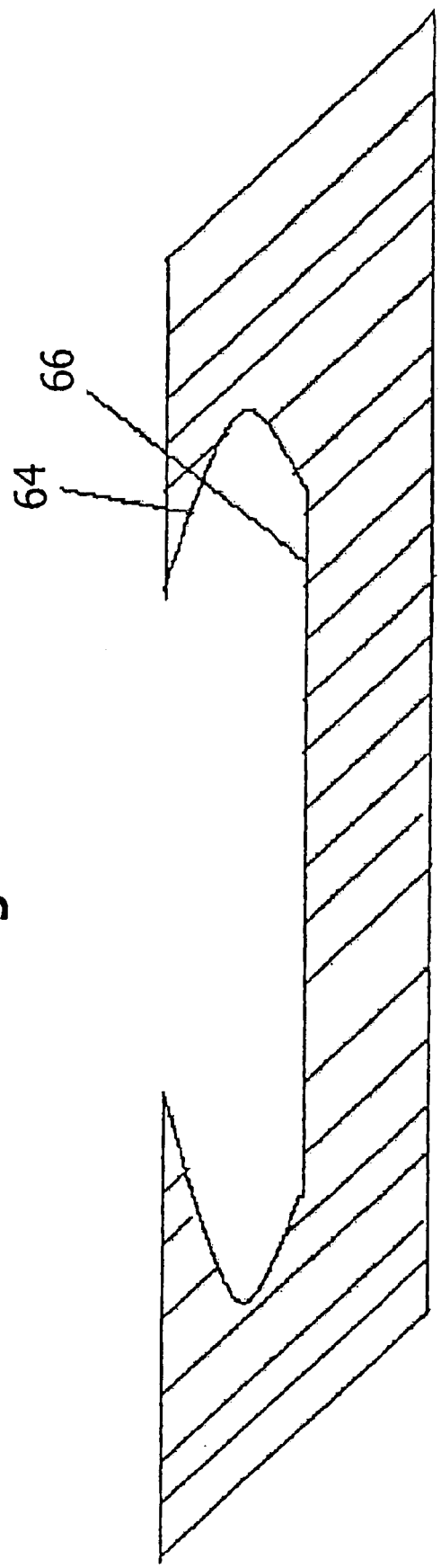

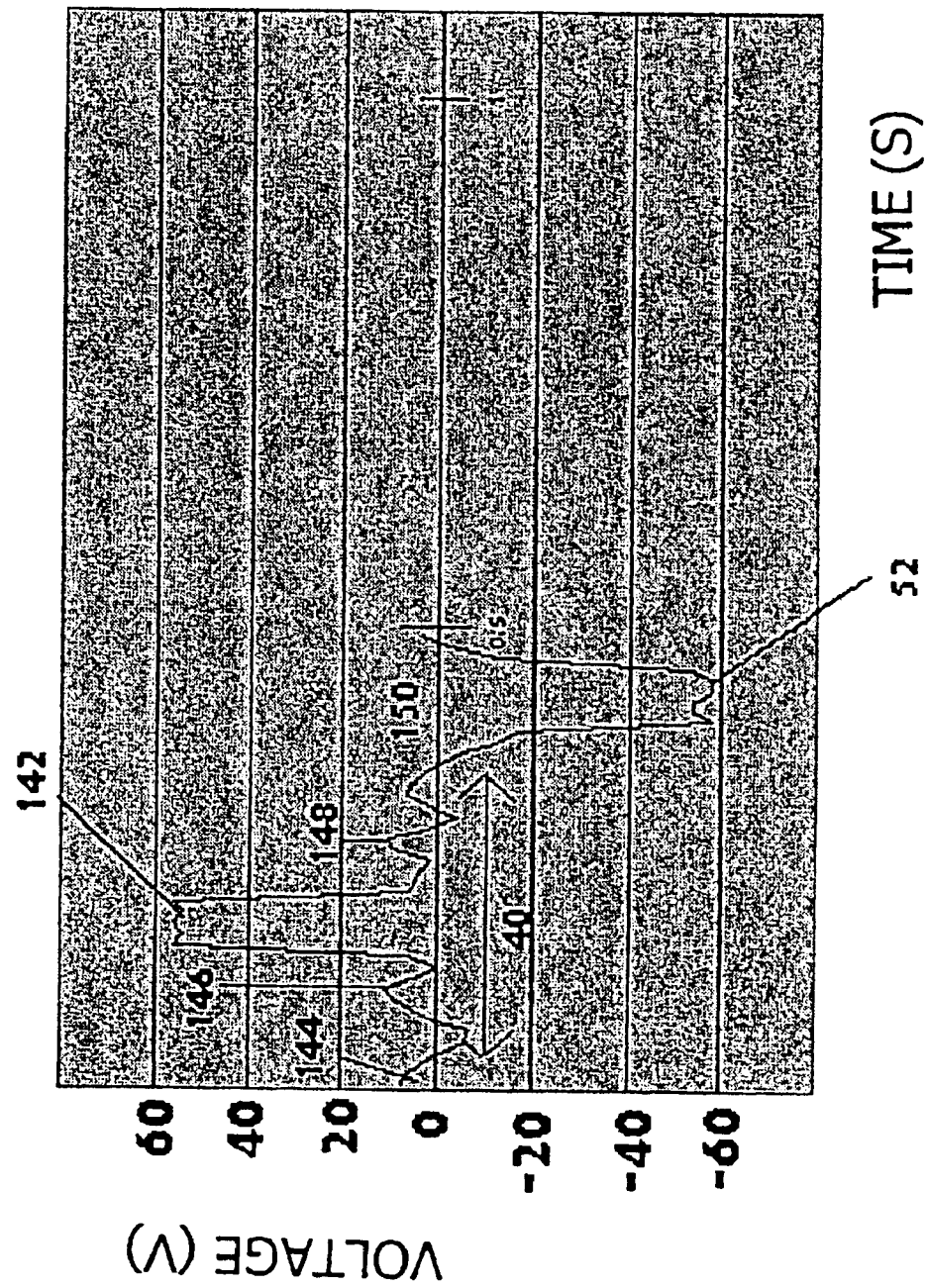

METHOD FOR THE TREATMENT OF BEDSORES USING ELECTRICAL IMPULSES

This application is a 371 of PCT/IL01/00502 May 30, 2001 which is a continuation of Ser. No. 09/584,488 filed Jun. 1, 2000 U.S. Pat. No. 6,393,326 and a continuation of Ser. No. 09/593,399 filed Jun. 14, 2000 now U.S. Pat. No. 6,363,284.

FIELD AND BACKGROUND OF THE INVENTION

The present invention relates to a method for promoting the healing of damaged animal tissue, including human tissue by propagation of an electric current flow through the tissue. In particular, the invention relates to a method and procedure for promoting the healing of chronic sores such as bedsores and the like by propagation of an electric current flow through the damaged tissue.

U.S. Pat. No. 4,117,846 to Williams discloses a disposable skin conducting electrode assembly and electrode therefor for use on a patient. The electrode assembly includes an electrolyte pad, an electrode and an adhesive pad.

It is taught in the above-mentioned patent that such an electrode can be used for various kinds of electrical treatments, including electrosurgery, medical diathermy (thermopenetration), and pain relief using transcutaneous nerve stimulation, aiding the setting and proper healing of broken bones and fractured vertebrae, and improving the curvature of the spine.

An electrode of this type can also be used for the transmission of an electrical impulse for directly stimulating a nerve or nerve pathway for restoring the physiological functions of a damaged nerve system. U.S. Pat. No. 4,117,846 teaches that an electrode assembly of this kind can be used to apply an electrical current for enhancing or promoting the healing of traumatized, injured or displaced tissue. The healing of bedsores or decubitis ulcers, surgical incisions, skin ulcerations, and lacerations is aided by long term application of high frequency current, and in some cases, by the application of low voltage DC current.

In contrast to U.S. Pat. No. 4,117,846, which mentions the application of high frequency current, U.S. Pat. No. 4,738,250 to Fulkerson, et al., discloses a medical electrical apparatus impressing a low frequency, bipolar, voltage wave form through spaced-apart electrodes, across a damaged area of living animal tissue to cause a low, bipolar, current to flow through the damaged area to increase the metabolic activity of viable cells in that area and hence to accelerate healing. The current flow is monitored and used to control the magnitude of the voltage wave to cause the magnitude of current flow to be within the desired parameters. The frequency, wave form and voltage of the impressed voltage-wave and the current flow are all below a level which can be damage typical living cells.

According to U.S. Pat. No. 4,738,250, the above-described increase in metabolic activity results in at least the following positive benefits: accelerated production of adenosine triphosphate (ATP), increased synthesis of cell protein, improved cell membrane transport system, and accelerated production of collagen.

U.S. Pat. No. 4,738,250 further discloses that this electrical treatment signal reduces the concentration of free radicals that appear when cells are damaged. These free radicals are known to cause further damage by cell membrane disruption; and this reduction, done in accordance with the teachings of the invention, tends to reduce or eliminate this continuing damage without the current flow itself damaging the cells or otherwise insulting the living tissue being treated.

The electrical treatment signal disclosed by U.S. Pat. No. 4,738,250 is characterized by a current within a range of about 20 to 900 microamperes, resulting in the voltage of the treatment signal to be within a range of from zero to 30 volts. It is further disclosed that currents between 20 and 600 microamperes give good results, and that optimal results are obtained between 500 and 600 microamperes. Current flows approaching 1000 microamperes or 1 milliampere have proved destructive to cells in the pathway of such flow.

U.S. Pat. No. 4,738,250 also teaches a treatment signal having a treatment signal frequency within a range of about 0.1 to 15 Hz. However, in contrast to this relatively wide frequency range of 0.1 Hz to 15 Hz, U.S. Pat. No. 4,738,250 further discloses that the frequency of the wave form used can be varied from a very low frequency to a frequency slightly less than 1 Hz. Good results were obtained between 0.1 Hz and 0.9 Hz, and optimal results were obtained using a frequency of 0.5 Hz.

The form of the wave form applied is bipolar. In a first embodiment of the invention, the voltage of the treatment signal is increased in a linear fashion during each treatment signal time period until the current of the treatment signal attains its preselected value; and in a second embodiment of the invention, the voltage is increased nonlinearly, in an exponential fashion, during each treatment signal time period until the current attains its preselected value.

It must be emphasized that U.S. Pat. No. 4,117,846 to Williams, focuses on the requisite hardware components of the electrode assembly for obtaining electrical impulses (for applying numerous and varied kinds of electrical treatments, from pain relief to electrosurgery) and not on an effective procedure for healing bedsores and the like.

Similarly, U.S. Pat. No. 4,738,250 to Fulkerson, et al., focuses on the components of the electrical medical instrument for obtaining electrical impulses. U.S. Pat. No. 4,738,250 also focuses on the proper range of various electrical wave properties that promote the healing of damaged areas of tissue, including voltage magnitude, current magnitude, signal frequency, etc. However, little emphasis is placed on the treatment procedure. The treatment activation period disclosed is within a range of about 20 seconds to 20 minutes, and it is taught that electrodes can be repositioned around different parts of the affected areas.

The sixty-fold span of the treatment activation period taught by U.S. Pat. No. 4,738,250—20 seconds to 20 minutes—is so broad that it is substantially devoid of practical guidance in administering the treatment. In practicing the prior art, the physician must resort to guessing the appropriate treatment period, which almost inevitably will result in an over-administering or an under-administering of the treatment. Furthermore, the treatment procedure may continue for days before the effectiveness of the treatment procedure becomes apparent.

Due to these and other deficiencies in the prior art, the treatment systems and methods described above have not been implemented in the treatment of bedsores, to the best of our knowledge. It may be stated with certainty that these prior art systems and methods are not common practice. It must be emphasized that there are no known, effective treatments for curing bedsores. According to T. McNamara, an expert in the prevention of amputation, treatment consists of wound management (keeping the affected area clean, administering antibiotics) combined with interventive procedures to improve the flow of blood, such as balloon angioplasty or bypass surgery (Dr. Thomas McNamara, "Non-Surgical Techniques to Heal Foot Ulcers, Prevent Amputation and Relieve Leg Pain", WebMD, 1999). Thus, the fact that the above-described systems and methods (applying electrical wave forms) have not been implemented is a clear indication of their ineffectiveness in the treatment of bedsores.

There is therefore a recognized need for, and it would be highly advantageous to have, an effective method and procedure for promoting the healing of bedsores and the like. Moreover, it would be of particular advantage to have a method that can provide simple and inexpensive treatment by the propagation of an electric current flow through the damaged tissue. It would be of further advantage to have an adaptive method that is tailored to the biofeedback from the body of the individual undergoing treatment. Finally, it would be highly advantageous to have a method that is mild and non-invasive, in view of the generally frail condition of those afflicted by bedsores.

SUMMARY OF THE INVENTION

According to one aspect of the present invention, there is provided a method for the treatment of a sore, the method including the steps of: (a) situating a pair of spaced-apart electrodes in contact with healthy tissue on opposite sides of a sore to be treated; and (b) externally inducing a percutaneous flow of electrical current between the electrodes by establishing an external bipolar voltage wave form across the electrodes at a frequency of between 2 Hz and 10 Hz, wherein the sore includes an area having substantially zero electrical activity.

According to further features in the described preferred embodiments, the sore is a bedsore.

According to further features in the described preferred embodiments, the frequency of the external bipolar voltage wave form across the electrodes is between 2 Hz and 5 Hz.

According to further features in the described preferred embodiments, the external bipolar voltage wave form includes a positive voltage half cycle and a negative voltage half cycle, wherein at least one of the positive voltage half cycle and negative voltage half cycle contains at least two peaks.

According to another aspect of the present invention, there is provided a method for treatment of a sore by applying a series of voltage wave forms, the method including the steps of: (a) situating a pair of spaced-apart electrodes in contact with healthy tissue on opposite sides of the sore, the sore including an area having substantially zero electrical activity; and (b) externally inducing a percutaneous flow of electrical current between the electrodes by establishing the series of voltage wave forms across the electrodes, wherein the series of voltage wave forms includes wave forms designed to substantially mimic characteristic natural voltage wave form emissions of at least one electrically active sore.

According to further features in the described preferred embodiments, the sore having substantially zero electrical activity is a bedsore.

According to further features in the described preferred embodiments, the series of voltage wave forms includes at least one bipolar wave form.

According to further features in the described preferred embodiments, the series of voltage wave forms includes at least one asymmetric wave form.

According to further features in the described preferred embodiments, the series of voltage wave forms has a peak rate of 50–10,000 peaks per second.

According to further features in the described preferred embodiments, the series of voltage wave forms has a peak rate of 200–5,000 peaks per second.

According to further features in the described preferred embodiments, the series of voltage wave forms has a peak rate of 400–2,000 peaks per second.

According to further features in the described preferred embodiments, the series of voltage wave forms includes at least one wave form having a voltage peak of 3–10 Volts.

According to further features in the described preferred embodiments, the at least one electrically active sore is a sore of the patient being treated.

According to further features in the described preferred embodiments, the at least one electrically active sore is a plurality of electrical active sores, and wherein the characteristic natural voltage wave form emissions include an average of voltage wave form emissions of the plurality.

According to further features in the described preferred embodiments, the treatment method further includes, prior to step (b): (c) providing the series of voltage wave forms, the series of voltage wave forms being derived from voltage wave form emissions of the at least one electrically active sore.

According to further features in the described preferred embodiments, the series of voltage wave forms further includes an external bipolar voltage wave form having a frequency of between 2 Hz and 30 Hz.

According to further features in the described preferred embodiments, the external bipolar voltage wave form has a frequency of between 2 Hz and 10 Hz.

According to still further features in the described preferred embodiments, the external bipolar voltage wave form has a frequency of between 2 Hz and 5 Hz.

According to still further features in the described preferred embodiments, the series of voltage wave forms is a substantially repetitive series.

According to another aspect of the present invention, there is provided a method for the treatment of sores including the steps of: (a) situating a pair of spaced-apart electrodes in contact with healthy tissue on opposite sides of a sore of a patient to be treated; (b) externally inducing and maintaining a percutaneous flow of electrical current between the electrodes by establishing at least one voltage wave form across the electrodes, and (c) monitoring the sore for an independent electrical activity, wherein the sore includes an area having substantially zero electrical activity.

According to further features in the described preferred embodiments, the area having substantially zero electrical activity is a bedsore.

According to still further features in the described preferred embodiments, the voltage wave form has a frequency between 2 Hz and 5 Hz.

According to still further features in the described preferred embodiments, the voltage wave form has a frequency between 16 Hz and 30 Hz.

According to still further features in the described preferred embodiments, the voltage wave form is bipolar.

According to still further features in the described preferred embodiments, the voltage wave form is of substantially cyclic form, the cyclic form including a positive voltage half cycle and a negative voltage half cycle, and wherein at least one of the positive voltage half cycle and negative voltage half cycle contains at least two peaks.

According to still further features in the described preferred embodiments, the percutaneous flow of electrical current is maintained for at least 5 minutes.

According to still further features in the described preferred embodiments, the percutaneous flow of electrical current is maintained for at least 25 minutes.

According to still further features in the described preferred embodiments, the independent electrical activity is characterized by a wave form, and wherein the treatment procedure further includes: (d) if the independent electrical activity is detected: setting the voltage wave form established across the electrodes to substantially match the wave form of the independent electrical activity, and (e) reapplying step (b).

According to still further features in the described preferred embodiments, the independent electrical activity is characterized by a wave frequency, and the treatment procedure further includes: (d) if the independent electrical activity is detected: setting the voltage wave form established across the electrodes to substantially match the wave frequency of the independent electrical activity, and (e) reapplying step (b).

According to still further features in the described preferred embodiments, the independent electrical activity is characterized by a wave intensity, and the treatment procedure further includes: (d) if the independent electrical activity is detected: setting the voltage wave form established across the electrodes to substantially match the wave intensity of the independent electrical activity, and (e) reapplying step (b).

According to still further features in the described preferred embodiments, the independent electrical activity is characterized by a wave form, a wave frequency, and a wave intensity, and the treatment procedure further includes: (d) if the independent electrical activity is detected: setting the voltage wave form established across the electrodes to substantially match the wave form, the wave frequency, and the wave intensity of the independent electrical activity, and (e) reapplying step (b).

According to still further features in the described preferred embodiments, the steps (b), (c), and (d) are reapplied until the independent electrical activity substantially resembles an independent electrical activity of healthy tissue.

According to still further features in the described preferred embodiments, the steps (b), (c), and (d) are reapplied for an entire duration of the treatment procedure.

According to still further features in the described preferred embodiments, the treatment method includes, prior to step (b): step (c) providing the at least one voltage wave form, the at least one voltage wave form being derived from voltage wave form emissions of at least one electrically active sore.

According to yet another aspect of the present invention, there is provided a method for the treatment of sores including the steps of (a) situating a pair of spaced-apart electrodes in contact with healthy tissue on opposite sides of a sore to be treated, the sore including an area having substantially zero electrical activity; (b) externally inducing and maintaining a percutaneous flow of electrical current between the electrodes by establishing an external voltage wave form across the electrodes; (c) monitoring the area for independent electrical activity, and (d) if the independent electrical activity is not sustained: reapplying step (b).

According to further features in the described preferred embodiments, step (d) is performed until the independent electrical activity is permanently sustained.

According to still further features in the described preferred embodiments, the independent electrical activity is sustained for at least 5 minutes after the percutaneous flow of electrical current is terminated.

According to still further features in the described preferred embodiments, the independent electrical activity is sustained for at least 30 minutes after the percutaneous flow of electrical current is terminated.

According to still further features in the described preferred embodiments, the independent electrical activity is sustained for at least 90 minutes after the percutaneous flow of electrical current is terminated.

According to still further features in the described preferred embodiments, at least one aspect of the independent electrical activity is reproduced and established across the electrodes for an entire duration of the treatment procedure, or for a substantial portion thereof.

The present invention successfully addresses the shortcomings of the existing technologies by providing a practical method for the treatment of bedsores and the like, in which the healing progress of the sore can be monitored and evaluated quickly and accurately. Consequently, the treatment can be directed and adapted according to the individual needs of the patient and the status of the sores.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3b shows the bedsore of FIG. 3a in a distorted state;

FIG. 4 is a graph illustrating an integrated voltage wave form according to the present invention;

DESCRIPTION OF THE PREFERRED EMBODIMENTS

Figure 1:
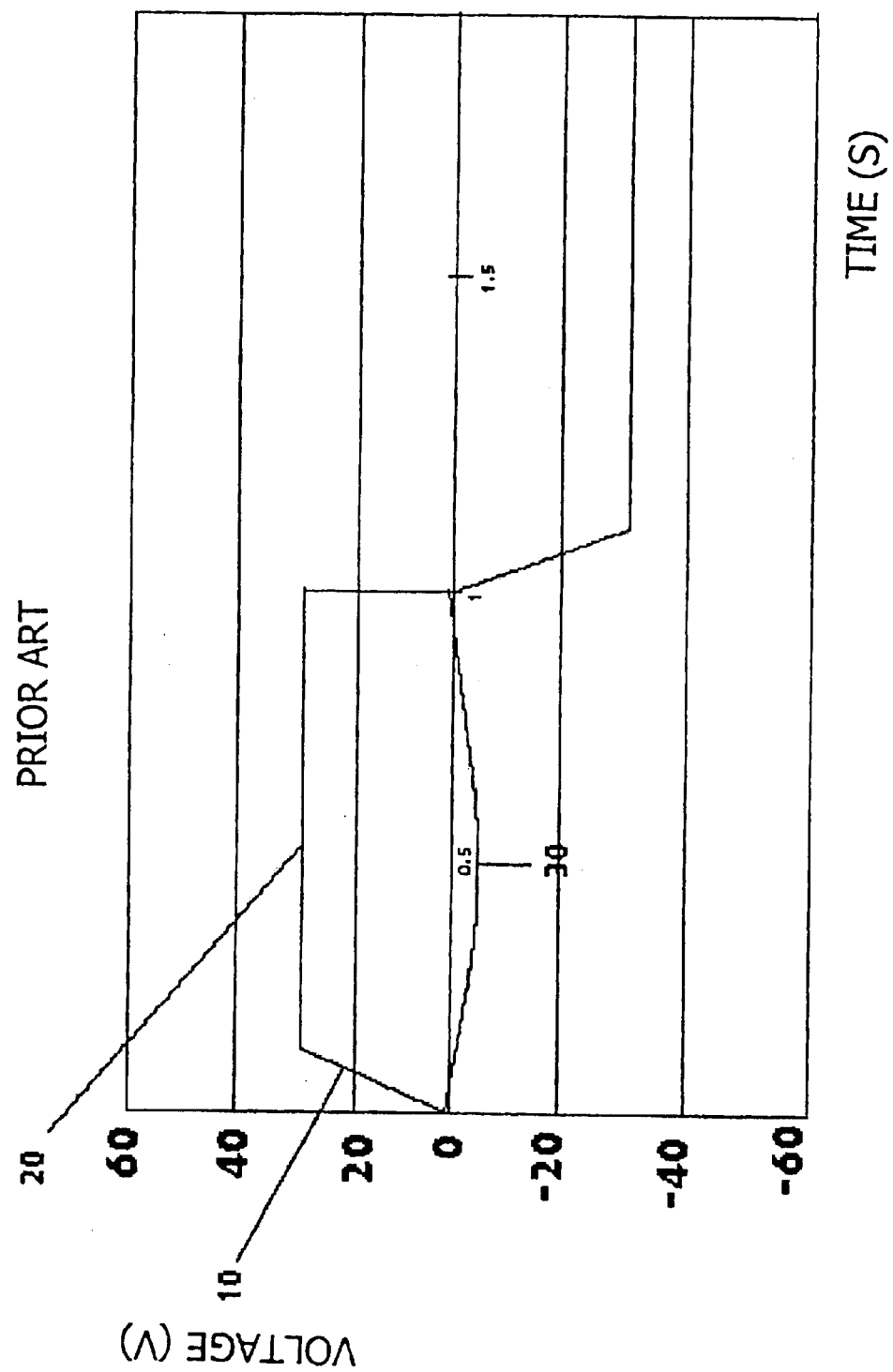
FIG. 1 is a graph illustrating an electrical wave form according to an optimal embodiment of the prior art.

The principles and operation of a method and procedure for promoting the healing of bedsores by propagation of an electric current flow through the damaged tissue, according to the present invention, may be better understood with reference to the drawings and the accompanying description.

Without wishing to be limited, the treatment mechanism is based on a discovery of how the body treats sores and maladies of various kinds. The brain sends electric signals through the nervous system to the various parts of the body. Special signals of a particular form and frequency are transmitted to areas identified as having damaged tissues. Although the frequency, shape, and intensity of the signals may vary from individual to individual, and from malady to malady, there is a very strong common denominator between them.

The information-gathering parts of the nervous system provide a tremendous amount of data, continually updated, about the condition of the body and its surroundings. The sense organs give a detailed picture of the outside world, but there are also many sensors within the body that monitor the activity and condition of the body. Some of these sensors, known as proprioreceptors, are found in muscles, joints, ligaments, and tendons. Proprioreceptors in the muscles, for example, inform the central nervous system about how much a muscle has contracted, and also register pain.

Other specialized sensors monitor the blood circulation, respiration and digestion. Baroreceptors measure blood pressure in the great arteries of the body, and chemoreceptors analyze the levels of oxygen and carbon dioxide in the blood. The lungs and airway contain stretch receptors, and the activity of the heart is monitored by specialized receptors in the atria and ventricles.

The sensors send messages to the central nervous system in the form of tiny electrical impulses. Each sensor is attached to a long fiber called a dendrite, which is a long extension of a nerve cell, or "axon". Each single nerve contains thousands of dendrites, which are collected together in bundles to make up a single nerve, and the whole complex stricture leads from the sensors to the spinal cord.

A cross-section of the spinal cord reveals a gray area in the middle, surrounded by white matter. The gray matter consists of nerve cells and their connections, and the white matter contains nerve fibers, many of which are arranged in tracts leading to specific locations in the brain. Information gathered by the various sensors of the body passes into the gray matter in the spinal cord, where it is organized according to type and then relayed through the above-mentioned nerve fiber tracts to the command centers of the central nervous system in the brain.

When a particular area of tissue has been damaged, the brain recognizes the "distress signals" conveyed from the local sensors, and supervises and directs the healing effort accordingly. The supervisory role of the brain includes a continual transmission of "instructions" as electrical impulses that are sent to the affected area and, if necessary, to other organs and parts of the body as well. These may include instructions to increase the blood supply to the affected area. It has been established by the inventor that bedsores behave in a completely different fashion than other types of sores, ulcers, and the like. In bedsores, the tissue, including nerve cells, is dead, such that all electrical activity has been completely interrupted. Because it is highly probable that the contact with the brain has been lost or greatly impaired, the healing effort is severely hampered, and consequently, the healing effort is performed in a more local, less organized fashion.

Moreover, communication via the central nervous system is not lost only in the area of the bedsore. Often, the communication break in the relatively small area of the bedsore triggers a gradual cessation of communication or electrical activity with other nervous pathways belonging to the same "relay station" of the nervous system. In some cases, particularly with the elderly and with people with weakened body defenses, a local bedsore can spread to the point that entire limbs need amputating.

Several discoveries of the inventor have led to the invention as described herein. By isolating patterned electrical activity of around areas using various measuring and filtering techniques, the inventor successfully measured and characterized electrical activities from numerous and different wounds (puncture wounds, cuts, burns, etc.) on numerous patients. Surprisingly, these electrical activities were found to have shared characteristic features (despite having a wide variance). These features are described in further detail hereinbelow.

It was further discovered by the inventor that chronic wounds such as bedsores do not have this unique electrical activity. Finally, it was discovered by the inventor that the electrical "language" of the body can be applied to such chronic sores to stimulate dead wounds into electrically-active areas, and ultimately, into normally-functioning skin.

It should be emphasized that all known prior art disclosed stimulations that represent arbitrary constructs of the inventors.

The electrical waves of one aspect of the present invention essentially mimic the waves that are normally produced by the brain and transmitted by the brain to damaged tissues. Because there is no electrical activity whatsoever coming from the brain, the present invention provides to the damaged area electrical signals that are substantially identical from an operational standpoint to those transmitted by the brain through the nervous system. The body "recognizes" the signal and provides the appropriate healing response. Eventually, vestiges of vitality return to the damaged area, and the electrical activity of the area is sustained without further external electrical stimulation. With communication restored along the nervous system pathway, the brain can again transmit electrical signals to the affected area, which indicates that the body is fundamentally capable of furthering the healing process on its own.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Referring now to the drawings, FIG. 1 is a graph of a voltage wave form according to the prior art, in which voltage (volts) is plotted versus time (seconds). U.S. Pat. No. 4,738,250 to Fulkerson et al. discloses a so-called "square wave" form wherein the voltage rises in a linear fashion 10 until a predetermined current flow is reached and then is maintained 20 until the end of a treatment signal time period which is the half cycle determined by the selected frequency. Thus, a frequency of 0.5 Hz corresponds to a cycle of 2 seconds, or a half cycle 30 of 1 second.

U.S. Pat. No. 4,738,250 also discloses a similar wave form, termed "modified square waves", wherein the voltage increases as an exponential function until the predetermined current flow reaches the predetermined level, and wherein the voltage is held at that level until the end of that half treatment signal time period.

The above-mentioned patent also teaches a treatment signal having a treatment signal frequency to be within a range of about 0.1 to 15 Hz. However, in contrast this relatively wide frequency range of 0.1 Hz to 15 Hz, the above-mentioned patent discloses that the frequency of the wave form used can be varied from a very low frequency to a frequency slightly less than 1 Hz. Good results were reported for frequencies between 0.1 Hz and 0.9 Hz, with optimal results being obtained at a frequency of 0.5 Hz.

The differences between the electrical waves of the present invention and those of the prior art are more fully appreciated when viewed in the context of the healing process in the body. Because the electrical waves of the present invention are very similar to the waves that are normally transmitted by the brain to damaged tissues, the body "recognizes" the signal and provides the appropriate healing response and support. Without wishing to be limited by the above theory, it has been discovered that by mimicking or substantially mimicking the form, intensity, and/or frequency of these "natural wave forms", the process of healing the sores is greatly improved. More particularly, the application of these "natural wave forms" has been found to be of critical importance in reviving the healing efforts of the body.

For this very reason, the shape of the electrical wave is of great importance. The straight or smooth wave forms disclosed by U.S. Pat. No. 4,738,250 do not resemble the waves that are normally produced by the brain and transmitted via the central nervous system, hence their effectiveness is extremely limited, despite the propagation of an electric field in the affected area.

As used herein in the specification and in the claims section that follows, the term "peak" refers to a portion of a voltage half cycle having an absolute maximum voltage followed by a slope in the direction of the zero voltage line.

As used herein in the specification and in the claims section that follows, the term "substantially cyclic voltage wave form" refers to a wave form, consisting of various peaks, which repeats itself. Although the wave form need not be identical from cycle to cycle, and small changes in the wave form may even be preferable, the general appearance of the wave form is repetitive.

As used herein in the specification and in the claims section that follows, the term "sores having substantially zero electrical activity" refers to a type of sore whose independent electrical activity is significantly below that of healthy tissue or non-festering sores, or whose electrical activity is substantially not independent electrical activity (i.e., without external and/or foreign stimulation). A bedsore is a common example of a sore having substantially zero electrical activity.

In the medical literature, the term "bedsore" refers to an area of skin damage, and often ulceration, that is highly correlated with a restriction of the blood supply to the affected area. The immediate cause of the blood restriction is usually constant pressure on the affected areas. As used herein in the specification and in the claims section that follows, the term "bedsore" refers to, but is not limited to, the above-described skin damage and ulcerations.

As used herein in the specification and in the claims section that follows, the term "independent electrical activity" refers to electrical activity that is sustained by the body without external or foreign stimulation.

As used herein in the specification and in the claims section that follows, the term "electrically active sore" refers to a sore having independent electrical activity, including, but not limited to, puncture wounds, cuts, and scrapes.

As used herein in the specification and in the claims section that follows, the term "voltage wave form emissions" refers to a voltage vs. time behavior of independent electrical activity produced by one or more electrically active sores. The term "average" with respect to voltage wave form emissions refers to a characterization of voltage wave form emissions that is derived from a plurality of individual voltage wave form emissions. The term "average" includes weighted averages of different kinds.

As used herein in the specification and in the claims section that follows, a wave form "designed to substantially mimic characteristic nature voltage wave form emissions" and the like refers to a wave form having at least one attribute derived from characteristic attributes of natural voltage wave form emissions from electrically active sores. These characteristic attributes typically include general wave shape and/or peaks per second. These characteristic attributes may further include general wave shape and/or peaks per second along with wave intensity (voltage) and/or bipolarity.

Figure 2:
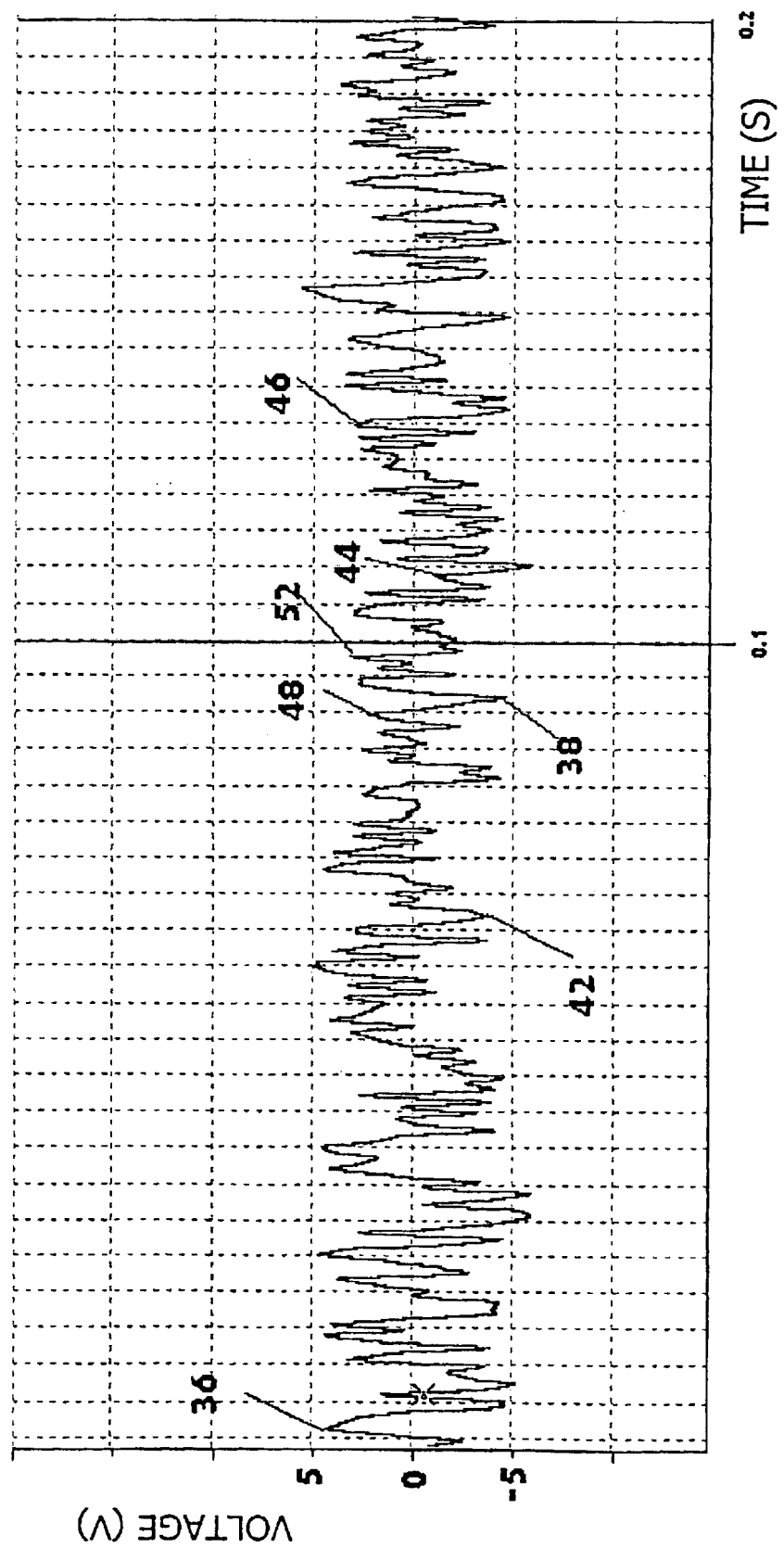
FIG. 2 is a graph illustrating a natural voltage wave form according to the present invention.

A typical graph of a series of natural wave forms, which, according to one aspect of the present invention, is propagated to areas containing bedsores and the like, is plotted in FIG. 2. The general form is bipolar, having positive voltage wave forms such as wave form 36 and negative voltage wave forms such as wave form 38. Most wave forms are substantially asymmetric, like wave form 36 and wave form 38. It is further evident from the plot that over approximately 0.20 seconds, there is a large number of wave forms, some of which are substantially single peaks ("singlet"s), such as wave form 42, others having substantially two peaks ("doublet"s), such as wave form 44, still others having three or more peaks ("multiplet"s) such as wave form 46. While it is difficult to characterize these wave forms and peaks, it is estimated that there are roughly 200 peaks (positive and negative) occurring over the span of 0.20 seconds, corresponding to about 1000 peaks per second. The present invention includes the use of wave forms having 50–10,000 peaks per second, and more preferably, wave forms having 200–5,000 peaks per second. It is presently preferred to have 400–2,000 peaks per second.

The duration of individual peaks varies greatly from peak to peak, with most peaks having a duration, measured at the baseline (V=0), of 0.0005 to 0.02 seconds. More typical peaks, such as peak 48 and peak 52, have a baseline width of 0.001 to 0.005 seconds.

In FIG. 2, the peak intensity, measured in Volts, is varied, but generally falls within the range of 0.1 to 5 Volts (absolute values). However, a series of natural wave form having the general form shown in FIG. 2, but having peak intensities of up to 40 Volts, and more preferably, up to 20 Volts has also been found to be effective. The actual voltage delivered to the affected area of the body is considerably lower, however, due to the impedance of the skin.

The difficulty in characterizing the wave forms of the present invention must be stressed. The importance and function of each wave form and the attributes thereof (intensity, shape, duration, etc.) are not well understood at present. What is clear, however, is that the body "recognizes" these wave forms and consequently, responds with a concentrated healing effort in the electrically-stimulated region.

In another aspect of the invention, there is provided a method for the treatment of sores including the steps of: (a)

situating, a pair of spaced-apart electrodes in contact with healthy tissue on opposite sides of an area containing cells to be treated, and (b) externally inducing a percutaneous flow of electrical current between the electrodes through the area by establishing an external bipolar voltage wave form across the electrodes at a frequency of between 2 Hz and 30 Hz, wherein the sores are sores having substantially zero electrical activity.

It was surprisingly discovered by the inventor that the most effective frequencies according to this aspect of the present invention lie in the range of 2–10 Hz, and most preferably in the range of 2–5 Hz.

Figure 3A:
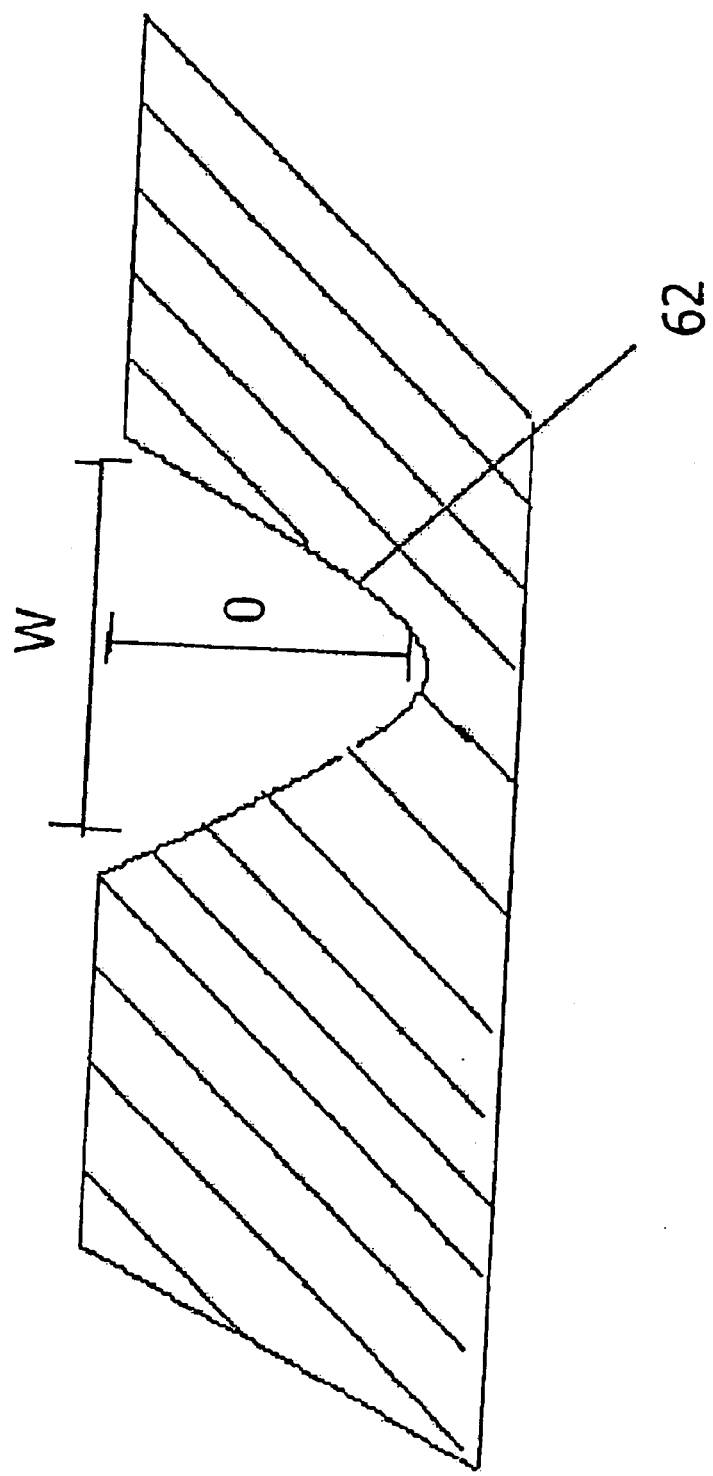
FIG. 3a is a schematic illustration of a bedsore.

This method has been found to be of particular efficacy in treating sores that extend, underneath the surface of the skin, beyond the perimeter of the open sore. As shown in FIG. 3a, bedsores and the like are often very deep, and may have a relatively large depth D to width W aspect ratio. Due to internal pressures underneath the sore, the bottom 62 of the sore is pushed towards the external surface of the skin, such that the sore acquires an oblong shape, as shown in FIG. 3b. Consequently, the bedsore develops a lip underneath the surface of the skin, consisting of two nearly juxtaposed skin surfaces 64,66. Skin surfaces 64,66 often carry a like charge, i.e., both surfaces 64,66 having a positive charge, or both surfaces 64,66 having a negative charge. As like charges repel, the healing of such sores in the region underneath the surface of the skin is often impeded.

The inventor has found that a bipolar wave form having a frequency of 2–5 Hz and a voltage of up to 60 Volts, is particularly effective in accelerating the healing process in the lip area of the bedsore. Without wishing to be bound by theory, it is believed that such a wave form neutralizes the charge of opposing skin surfaces 64,66, eliminating thereby a major obstacle to the bonding and healing process. It would appear that a unipolar wave form could also achieve this result, provided that the charge on opposing skin surfaces 64,66 is known. Practically, however, it is clearly easier to provide a bipolar wave form that effectively neutralizes any like charge (i.e., either positive or negative) on opposing skin surfaces 64,66.

In one preferred embodiment of the present invention, the bipolar wave form for accelerating the healing process in the lip area of the bedsore is integrated with natural-type wave forms of the variety depicted in FIG. 2. The integrated signal shown in FIG. 4 has one major peak 142 in the positive half cycle 140 and one major peak 152 in the negative half cycle 150. The major peaks have an absolute voltage of 50–60 Volts. The actual voltage delivered to the affected area of the body is considerably lower, however, due to the impedance of the skin. Several smaller peaks 144,146,148 with voltages ranging from 5–20 Volts appear in the positive half cycle 140. It should also be noted that the duration of the positive half cycle 140 and the duration of the negative half cycle 150 are not equal. The positive half cycle 140 lasts for about 0.4 seconds, while the negative half cycle 150 lasts for only about 0.1 seconds.

In another preferred embodiment of the present invention, the bipolar wave form for accelerating the healing process in the lip area of the bedsore is integrated with natural-type wave forms of the variety depicted in FIG. 2. In this embodiment, illustrated in FIG. 5, there are at least several hundred peaks of extremely short duration (~1,000 peaks per second) that separate between the artificial wave forms 70,72. It can be seen that the absolute voltage of artificial wave forms 70,72 has a magnitude approximately 2–5 times the absolute voltage of the interceding natural wave forms.

Figure 5:
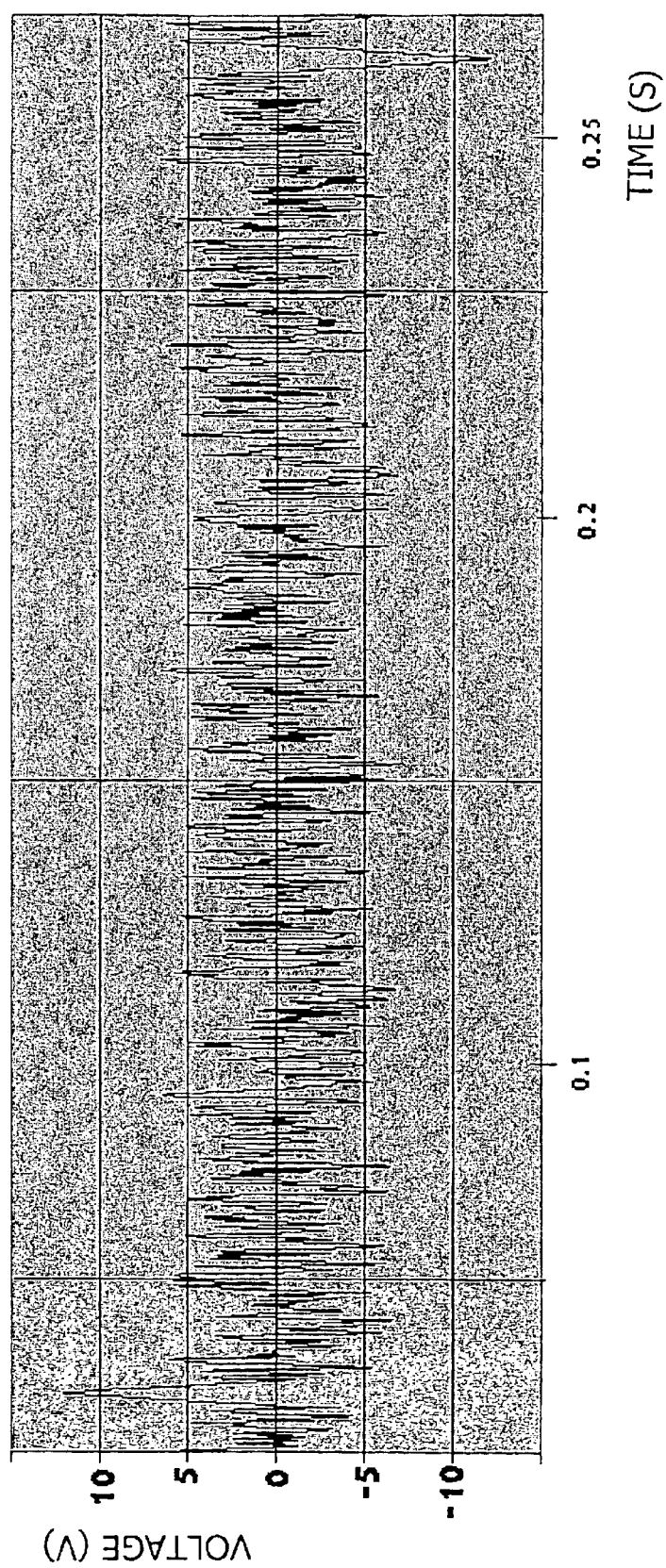
FIG. 5 is a graph illustrating an integrated voltage wave form according to a preferred embodiment of the present invention.
Figure 6:
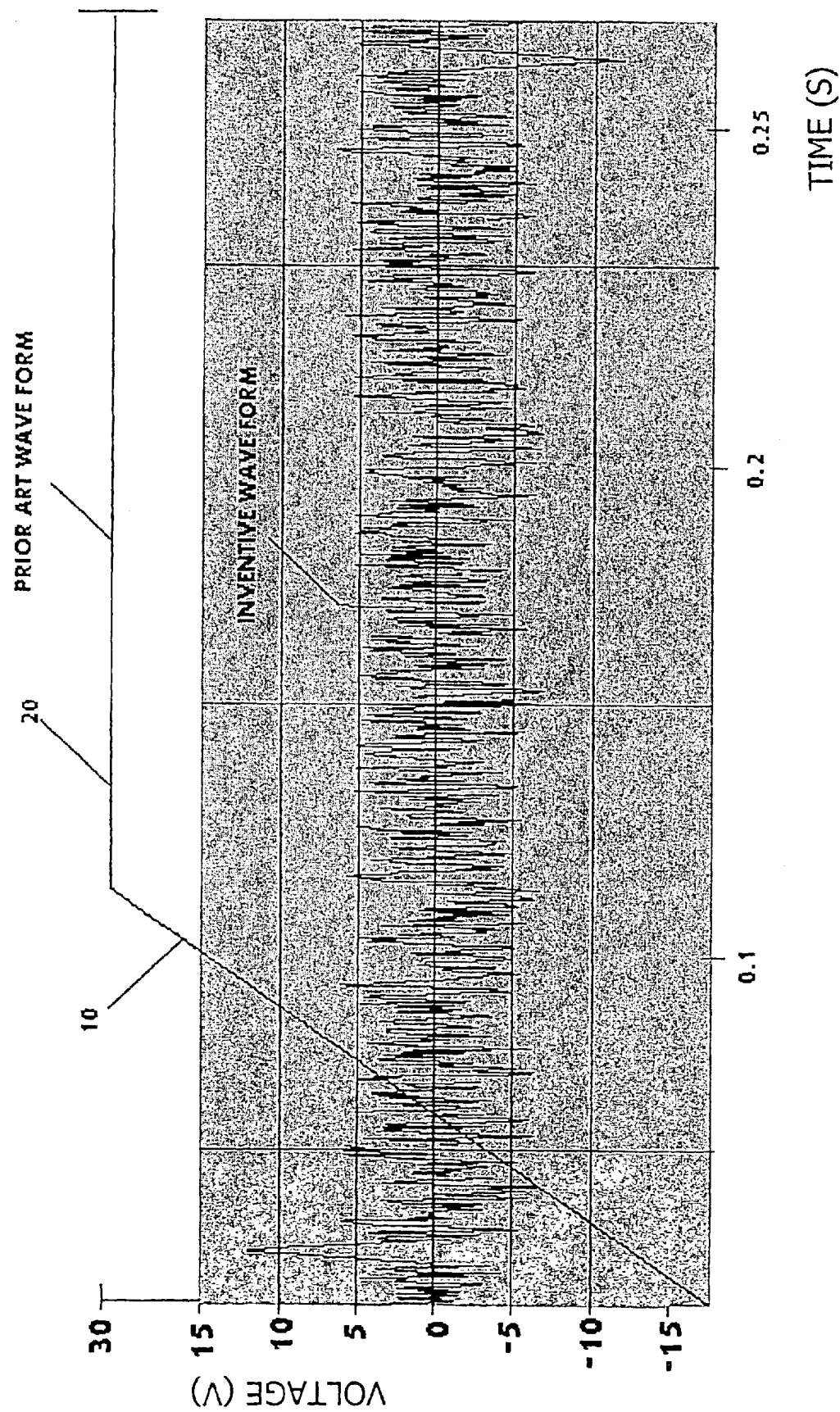
FIG. 6 is a graph in which the optimal prior art wave form of FIG. 1 is compared with a preferred embodiment of the inventive wave form.

FIG. 6 is a graph in which the typical wave form of the present invention, provided in FIG. 5, is compared with a portion of the optimal wave form according to the prior art, provided in FIG. 1. The width of the individual peaks in this preferred wave form of the present invention are about $\frac{1}{200}$ to $\frac{1}{1000}$ of the peak width in the wave form of the prior art.

Thus, it has been established by the inventor that the absence of electrical activity is the salient characteristic of bedsores and other festering sores that do not heal or heal very slowly. Moreover, it has been established by the inventor that electrical activity can gradually be restored to the affected areas by applying an electrical wave having a particular form and intensity.

It is manifestly evident from all of the above, that the wave forms according to the present invention are not necessarily symmetric in terms of the peak shapes, peak intensities, and the duration of the positive and negative half cycles. Moreover, these characteristics may also change somewhat from cycle to cycle. These minor chances are an attempt to reflect wave forms that are typically transmitted through the central nervous system to damaged tissues in the body. Without wishing to be limited, it is believed that these deviations from symmetrical wave forms actually promote healing, because the body "recognizes" the signal as coming from the central nervous system and hence responds faster and with a higher level of activity.

As described above, the sixty-fold span of the treatment activation period taught by U.S. Pat. No. 4,738,250—20 seconds to 20 minutes—is so broad that is substantially devoid of practical guidance in administering the treatment. In practicing the prior art, the physician must resort to guessing the appropriate treatment period, which almost inevitably will result in an over-administering or an under-administering of the treatment. Furthermore, the treatment procedure may continue for days before the effectiveness of the treatment procedure becomes apparent.

By sharp contrast, it has been discovered by the inventor that the healing process of such sores can be effectively monitored by measuring the electrical activity of the affected area after terminating the electrical impulse. A sore that responds to the electrical impulse treatment will continue to exhibit electrical activity for a period of time after the electrical impulses from the external and/or foreign source have been terminated. The duration of that time period is a powerful indication of the state of the sore, and of the healing progress of the sore. Hence, the present invention provides a quick and accurate means of "listening" to the sore under treatment and evaluating the healing progress.

Thus, according to the present invention there is provided a method for the treatment of sores including the steps of: (a) situating a pair of spaced-apart electrodes in contact with healthy tissue on opposite sides of an area containing cells to be treated, (b) externally inducing and maintaining a percutaneous flow of electrical current between the electrodes through the area by establishing an external voltage wave form across the electrodes, and (c) monitoring the area for independent electrical activity, wherein the sores are sores having substantially zero electrical activity.

In a preferred embodiment, the percutaneous flow of electrical current is maintained for at least 5 minutes, more preferably for at least 15 minutes, and most preferably for at least 25 minutes.

The information, or biofeedback, obtained from monitoring the electrical activity of the sore, particularly after electrical stimulation, can be utilized in various ways to those skilled in the art. One particularly beneficial way is a treatment method, discovered by the inventor, in which the independent electrical activity of the sore is monitored (i.e., activity after terminating the electrical stimulation) to determine the duration of the independent electrical activity. When the level of electrical activity is reduced below a certain level, the percutaneous flow of electrical current is reapplied. Upon terminating the flow of electrical current, the independent electrical activity is monitored once more, and the duration of the independent electrical activity is measured. Each time the level of electrical activity is reduced below a certain level, electrical stimulation is reapplied. Eventually, the area of damaged tissue sustains permanent electrical activity.

Without wishing to be limited, it is believed that such permanent electrical activity reflects a rejuvenated connection of the damaged area to the central nervous system, and provides a strong indication that the sore condition has improved and now resembles non-festering sores that the body is accustomed to healing. At this point, conventional wound management treatments (cleaning, anti-biotics, etc.) are generally sufficient to help the body revitalize the area into healthy tissue.

Hence, the present invention makes it possible to "converse" with the sore under treatment and thereby adapt the treatment activation period, the number of treatment periods, and other treatment parameters to the specific needs of the sore under treatment.

Thus, according to this aspect of the present invention there is provided a method for the treatment of sores including the steps of: (a) situating a pair of spaced-apart electrodes in contact with healthy tissue on opposite sides of a sore to be treated, (b) externally inducing and maintaining a percutaneous flow of electrical current between the electrodes by establishing an external voltage wave form across the electrodes, (c) monitoring the sore for independent electrical activity, and (d) if the independent electrical activity is not sustained: reapplying step (b), wherein the sores include a sore area having substantially zero electrical activity.

In a preferred embodiment, the independent electrical activity is sustained for at least 5 minutes after the percutaneous flow of electrical current is terminated.

In another presently-preferred embodiment, the independent electrical activity is sustained for at least 30 minutes after the percutaneous flow of electrical current is terminated, more preferably, 60 minutes, and most preferably 90 minutes.

In a preferred embodiment, step (d) is performed until the independent electrical activity is permanently sustained.

As used herein in the specification and in the claims section that follows, the term "permanently sustained electrical activity" and the like refer to two-way electrical activity between the central nervous system and the affected area, the electrical activity being sustained by the body without external or foreign stimulation and closely resembling the uninterrupted, lasting electrical activity of healing or healthy tissue.

An example of such a treatment procedure is provided in Examples 1–2 below.

EXAMPLES

Reference is now made to the following examples, which together with the above description, illustrate the invention in a non-limiting fashion.

Example 1

Upon discovering that a bedsore is absolutely devoid of electrical activity, the above-described clinical procedure was tested on a patient suffering from bedsores. The initial reading of electrical activity in and around the bedsore was zero, i.e., below the sensitivity of the measuring instrument. The affected area was electrically stimulated by externally inducing a percutaneous flow of electrical current between two electrodes through the damaged area. The voltage waves were of the form of the wave according to one embodiment of the present invention, illustrated in FIG. 4. The duration of the electrical stimulation was 20 minutes.

It was discovered by the inventor that the electrical fields in and around the damaged area continued to maintain electrical activity, on the order of microvolts, after ceasing the external electrical stimulation. These electrical fields were very similar to typical electrical fields of sores that heal readily without external intervention. With time, however, the magnitude of the electrical field decayed, such that after about 1.5 hours, the electrical activity dropped back to zero.

At this point, an additional 20 minute treatment was initiated, the additional treatment being substantially identical to the first electrical treatment. Upon ceasing the external electrical stimulation, the independent electrical activity was monitored once again. As before, the damaged area continued to display electrical activity, on the order of microvolts, this time lasting for over 2.5 hours before decaying to zero activity.

With each successive treatment using electrical stimulation, the independent electrical activity of the damaged area lengthened, and after the eleventh of such treatments, the electrical activity was permanently sustained.

Example 2

The above-described clinical procedure was tested on a patient suffering from bedsores. The initial reading of electrical activity in and around the bedsore was zero, i.e., below the sensitivity of the measuring instrument. The affected area was electrically stimulated by externally inducing a percutaneous flow of electrical current between two electrodes through the damaged area. The pre-programmed series of voltage waves were substantially identical to that of the embodiment illustrated in FIG. 5. The duration of the electrical stimulation was 20 minutes. The healing rate was relatively rapid, even with respect to the healing rate achieved using the series of wave forms utilized in Example 1.

Example 3

Pressure wounds were treated according to conventional hospital practice and using standard products such as saline-soaked gauze, Granoflex and Granogek bandages, Tender wet and Sofratolle products. These practices and products were applied to both placebo and positively-treated patients.

In addition, positively-treated patients were subjected to the following method according to the present invention. During the initial 7 days of treatment, patients were subjected to 3 treatments of 20 minutes each, at intervals of 8 hours. During the following 49 days, patients where subjected to 2 treatments of 20 minutes each, with a minimum of 6 hours between successive treatments. The pre-programmed series of voltage waves were substantially identical to that of the embodiment illustrated in FIG. 5.

The removal of bandaging was not necessary.

Placebo patients were subjected to the same routine as the positively-treated patients, including the attachment of electrodes, etc., but no electrical current was applied.

Figure 7:
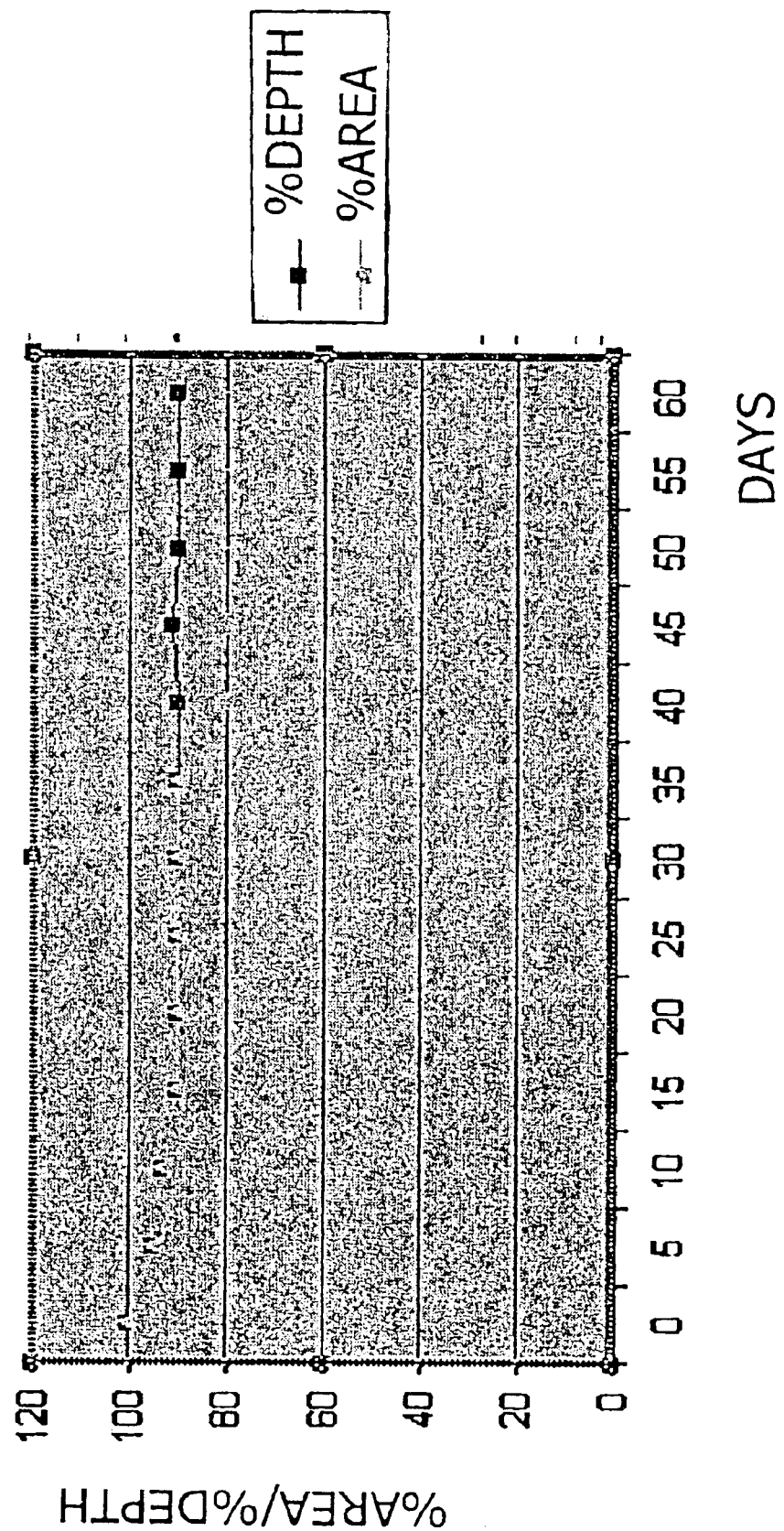
FIG. 7 illustrates the effect of conventional pressure sore treatments on the area and depth of a sore.
Figure 8:
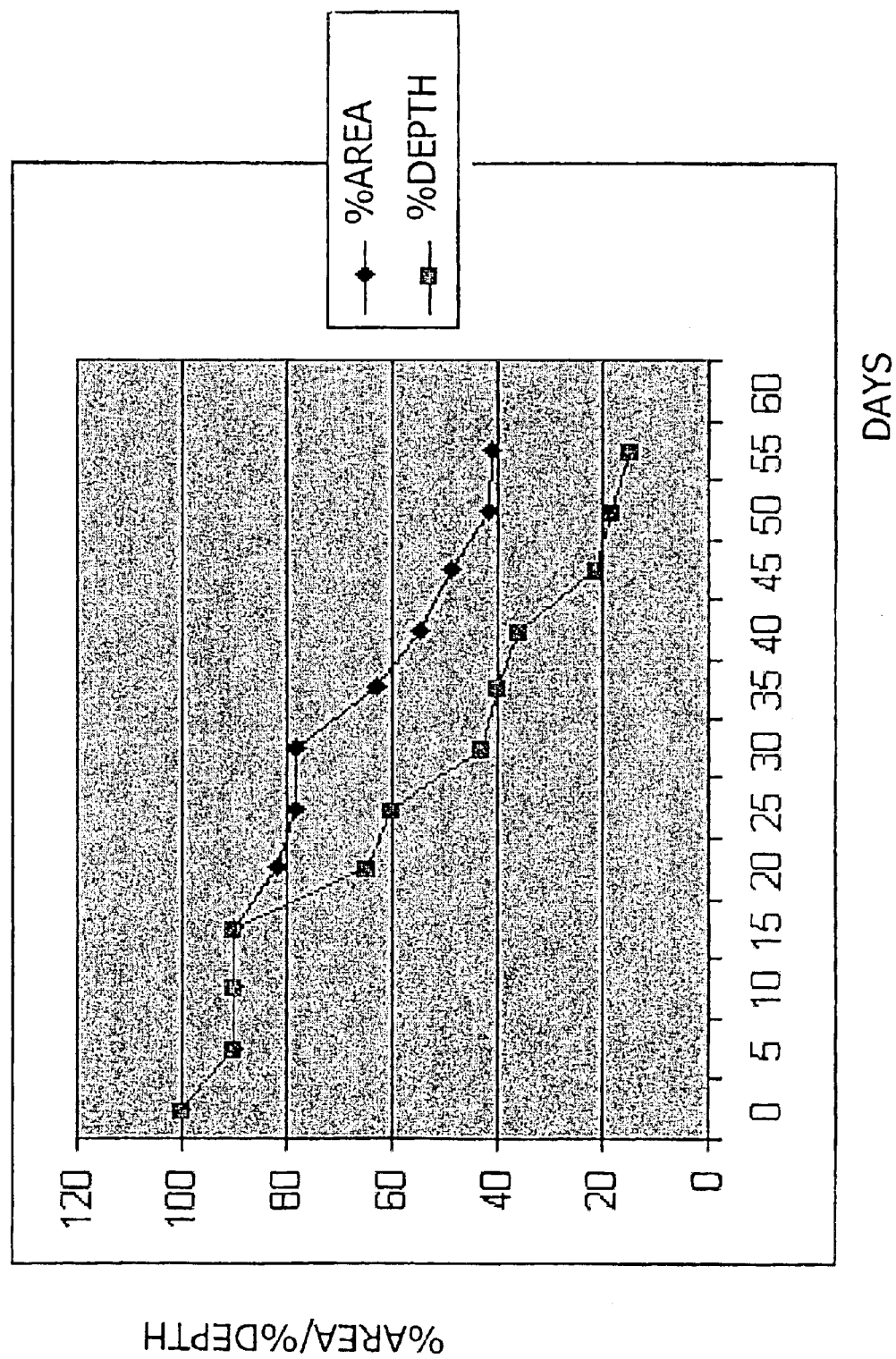
FIGS. 8–9 illustrate typical results obtained on patients subjected (in additional to conventional pressure sore treatments) to a treatment method of the present invention.
Figure 9:
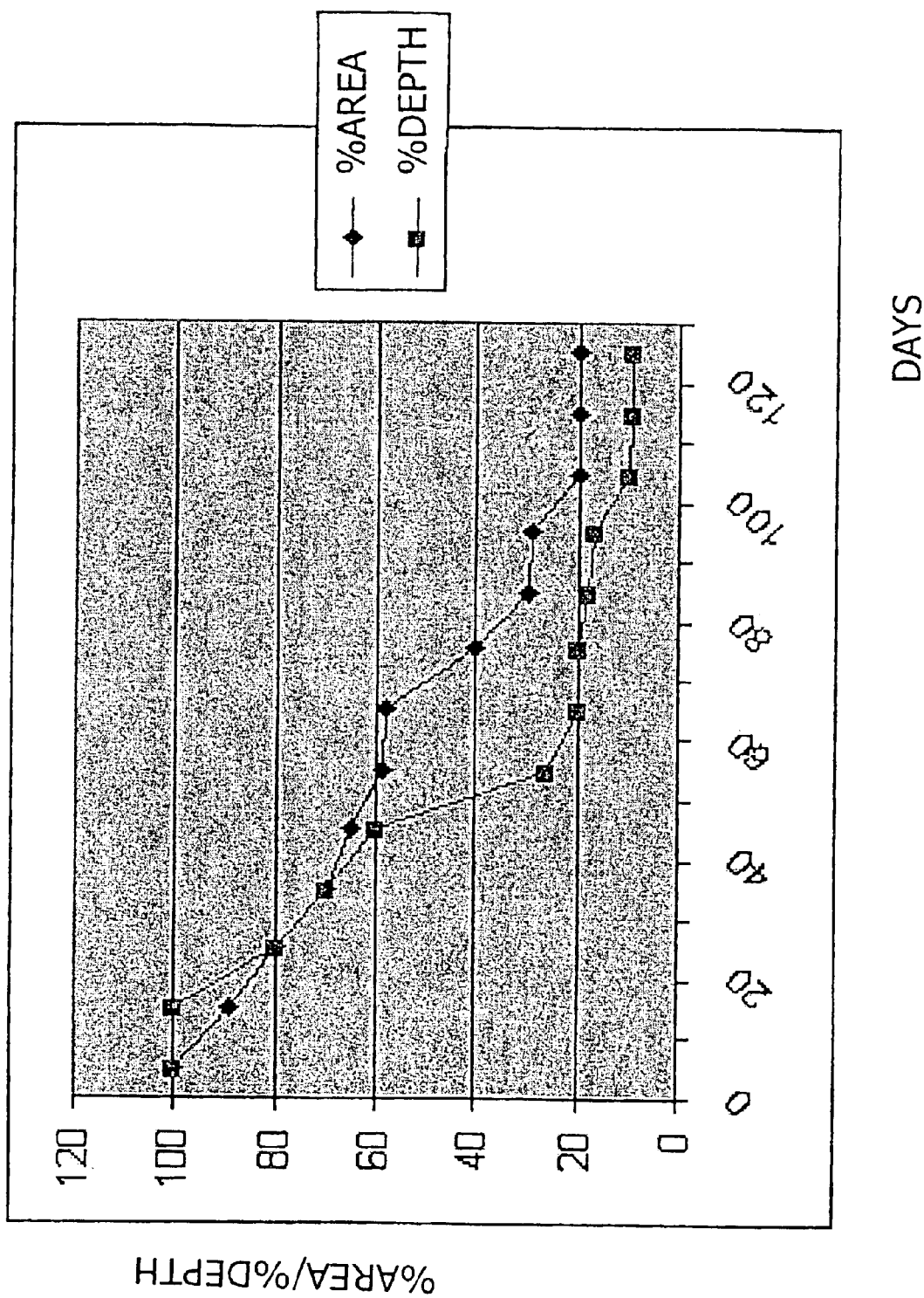

Results are provided in FIGS. 7–9, in which the area and depth of the sore are plotted vs. time. Both the area and the depth are normalized as percentages of the initial value of the sore area and sore depth, respectively.

In FIG. 7, a typical result for a placebo patient is provided. After 30 days of conventional treatments, there is substantially no improvement in the sore area and sore depth. After 56 days, the sore area was reduced to about 80% of the initial area; the sore depth remained substantially the same, about 90% of the original sore depth.

FIGS. 8–9 illustrate typical results obtained on patients subjected (in additional to the conventional treatments) to the above-described treatment method of the present invention. In FIG. 8, after 30 days of the inventive treatments, there is marked improvement in both the sore area—70% of the original area—and sore depth—45% of the original depth. After 53 days, the sore area was reduced to about 40% of the initial area; the sore depth was reduced to about 20% of the initial sore depth.

It must be stressed that even if total closure is not achieved within the 56 day treatment period, normal healing continues with no further need of treatment until closure of the sore.

This is shown in FIG. 9, in which the sore area and depth (of a different patient) drop to 20% and 10% of their initial values, respectively, after about 100 days after beginning the treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for the treatment of a sore, the method comprising the steps of:
    (a) situating electrodes in a vicinity of the sore of a patient to be treated, and
    (b) externally inducing a percutaneous flow of electrical current between said electrodes by establishing at least one voltage wave form across said electrodes, wherein said at least one voltage wave form includes a wave form designed to substantially mimic characteristic natural voltage wave form emissions of at least one electrically active sore.

2. The method of claim 1, wherein the sore includes an area having substantially zero electrical activity.

3. The method of claim 1, wherein said at least one voltage wave form includes at least one asymmetric wave form.

4. The method of claim 1, wherein said at least one voltage wave form has a peak rate of 50–10,000 peaks per second.

5. The method of claim 4, wherein said at least one voltage wave form has a peak rate of 200–5,000 peaks per second.

6. The method of claim 4, wherein said at least one voltage wave form has a peak rate of 400–2,000 peaks per second.

7. The method of claim 1, wherein said at least one voltage wave form includes at least one wave form having a voltage peak of 3–10 Volts.

8. The method of claim 1, wherein said at least one electrically active sore is a sore of said patient.

9. The method of claim 1, wherein said at least one electrically active sore is a plurality of electrically active sores, and wherein said characteristic natural voltage wave form emissions include an average of voltage wave form emissions of said plurality.

10. The method of claim 1, further comprising, prior to step (b):
    (c) providing at least one voltage wave form, said at least one voltage wave form being derived from voltage wave form emissions of said at least one electrically active sore.

11. The method of claim 10, wherein said at least one voltage wave form further includes an external bipolar voltage wave form having a frequency of between 2 Hz and 30 Hz.

12. The method of claim 11, wherein said external bipolar voltage wave form has a frequency of between 2 Hz and 10 Hz.

13. The method of claim 12, wherein said at least one voltage wave form is a substantially repetitive series.

14. The method of claim 11, wherein said external bipolar voltage wave form has a frequency of between 2 Hz and 5 Hz.

15. A system for the treatment of a sore of a patient, the system comprising:
    (a) electrodes for situating in a vicinity of the sore of the patient, and
    (b) a signal generator, for connecting to a power source, said signal generator for generating electrical impulses to said electrodes so as to induce a percutaneous flow of electrical current between said electrodes by establishing at least one voltage wave form across said electrodes,
    said at least one voltage wave form including a wave form designed to substantially mimic characteristic natural voltage wave form emissions of at least one electrically active sore.

16. The system of claim 15, wherein said signal generator further includes:
    a mechanism for applying a pre-programmed series of voltage waves via said electrodes.

17. The system of claim 16, wherein said pre-programmed series of voltage waves has a peak rate of 50–10,000 peaks per second.

18. The system of claim 17, wherein said is 200–5,000 peaks per second.

19. The system of claim 17, wherein said peak rate is 400–2,000 peaks per second.

20. The system of claim 15, wherein said wave form is bipolar.

21. A system for the treatment of a sore of a patient, the system comprising:
    (a) electrodes for situating in a vicinity of the sore of the patient, said sore including an area having substantially zero electrical activity, and
    (b) a signal generator, for connecting to a power source, said signal generator for generating electrical impulses to said electrodes so as to induce a percutaneous flow of electrical current between said electrodes by establishing at least one voltage wave form across said electrodes, said at least one voltage wave form having a peak rate of 50–10,000 peaks per second,
wherein said voltage wave form is derived from a voltage wave form emission of at least one electrically active sore.

22. The system of claim 21, wherein said voltage wave form is a bipolar voltage wave form.

23. The system of claim 21, wherein said peak rate of said voltage wave form is 200–5,000 peaks per second.

24. The system of claim 21, wherein said peak rate of said voltage wave form is 400–2,000 peaks per second.

25. The system of claim 21, wherein said signal generator further includes:
(c) a mechanism for applying a pre-programmed series of voltage waves via said electrodes.

26. The system of claim 21, the system further comprising:
(c) a mechanism for monitoring an independent electrical activity of the sore.

27. The system of claim 26, wherein said signal generator is designed and configured to generate said electrical impulses to said electrodes based on said independent electrical activity.

28. A system for the treatment of a sore of a patient, the system comprising:
(a) electrodes for situating in a vicinity of the sore of the patient, said sore including an area having substantially zero electrical activity, and
(b) a signal generator, for connecting to a power source, said signal generator for generating electrical impulses to said electrodes so as to induce a percutaneous flow of electrical current between said electrodes by establishing at least one voltage wave form across said electrodes,
wherein said voltage wave form is derived from a voltage wave form emission of at least one electrically active sore.

* * * * *